United States Patent [19]

Bradford

[11] Plant 4,425

[45] Jun. 12, 1979

[54] PEPEROMIA PLANT (AUTUMN LEAF)

[76] Inventor: Virginia Bradford, P.O. Box 1547, Winter Garden, Fla. 32787

[21] Appl. No.: 885,108

[22] Filed: Mar. 9, 1978

[51] Int. Cl.[2] ..... A01H 5/00

[52] U.S. Cl. ..... Plt./88

[58] Field of Search ..... Plt./88

*Primary Examiner*—Robert E. Bagwill
*Assistant Examiner*—James R. Feyrer
*Attorney, Agent, or Firm*—Duckworth, Hobby, Allen & Pettis

[57] ABSTRACT

A sport of a *Peperomia caperata* (Emerald Ripple) characterized by a mottled and variegated coloration of forest-olive and pale greens.

1 Drawing Figure

1

BACKGROUND

The present invention relates to a new and distinct variety of Peperomia Plant which was discovered by me in the greenhouses of Deer Run Nursery, Inc. in Winter Garden, Fla. as a sport of *Peperomia caperata* (Emerald Ripple). At the time of my discovery, my attention was attracted to three particular plants grown from the parent stock which were being grown under my direction and control, and which three plants appeared to be quite different from the parent variety by the coloration of the leaves. In particular, the leaves of these three plants were mottled and variegated with respect to the normal coloration of the leaves of the parent *Peperomia caperata* (Emerald Ripple). This variegation distinguishes the sport from the parent as well as other Peperomia varieties with which I am familiar.

The sport includes a center chocolate coloration extending out from the petiole a slight distance on the newly mature and younger mature leaves. As the foliage of the sport further matures, the chocolate center coloration disappears and the forest green coloration becomes dominant.

Asexual reproduction of my new Peperomia variety was performed from leaf cuttings taken from the three plants at Winter Garden, Fla., and this reproduction shows that the characteristics and distinctions of the sport are fixed and established and come through succeeding propagations.

DRAWING

The accompanying color photographs show a typical specimen plant of my new Peperomia variety and in color as nearly as it is reasonably possible to make the same in a color photograph of this character.

DETAILED DESCRIPTION OF THE PLANT

The following is a detailed description of my new Peperomia variety as based on my observations of specimen plants grown in Winter Garden, Fla., with color terminology in accordance with *Exotica* Horticultural Color Guide, Series 3, Ninth Edition, Roehrs Company, Inc., East Rutherford, N. J., 07073, printed in the United States.

Parentage: Sport of *Peperomia caperata* (Emerald Ripple).

Propagation: Holds its distinguishing leaf colorations through succeeding propagations by leaf or stem cuttings.

2

PLANT

This sport is substantially like its parent form in vegetative characteristics, including the corrugated, quilted leaf, except that the coloration of the leaf is mottled and variegated with respect to the customary dark green appearance of the parent. The vegetative characteristics of the sport are described below.

Origin: Mutation.
Parentage: *Peperomia caperata* (Emerald Ripple).
Classification: Piperaceae.
Form: Herbaceous.
Height: 6–8 inches.
Growth: Low, bushy house plant.
- *Leaves.*—25–35 per stalk.
- *Stems.*—2–5 inches long, ¼ inch at the base, branching from short, sturdy stalks.

Foliage: Abundant in quantity. One (1) leaflet per stem. Petiole arises from basal stem.
- *Leaf size.*—On a single plant, the mature leaves are generally 1.5 to 2.25 inches long and 1.25 to 2 inches wide.
- *Leaf shape.*—Roundish or heart-shaped, peltate, deeply corrugated and quilted, slightly undulate on margins.
- *Ribs and veins.*—Pronounced on underside, palmate.

Color:
- *Upper side.*—Mottled and variegated with Forest Green, #77 × Olive Green, #84 and Pale Green #72. Center, extending out from petiole, Chocolate #7.
- *Under side.*—Seafoam Green #71. Petioles. Pink (striped with Ruby Red #33).

THE FLOWER

Blooming habit: January to May.
Borne: Unbranched spike.
Size: Spike 4–8 inches tall, flowering part 2 inches.
Shape: Spike erect.
Petalage: Insignificant.
- *Texture.*—slightly sticky.
- *Appearance.*—Greenish, white color. Spike pendulous when past.
- *Persistence.*—2 weeks.

Petaloids: Apetalous.
Discoloration: None.
Fragrance: None.

I claim:

1. A new and distinctive variety of Peperomia plant substantially as herein shown and described, characterized by a variegated leaf mottled with dark and light green.

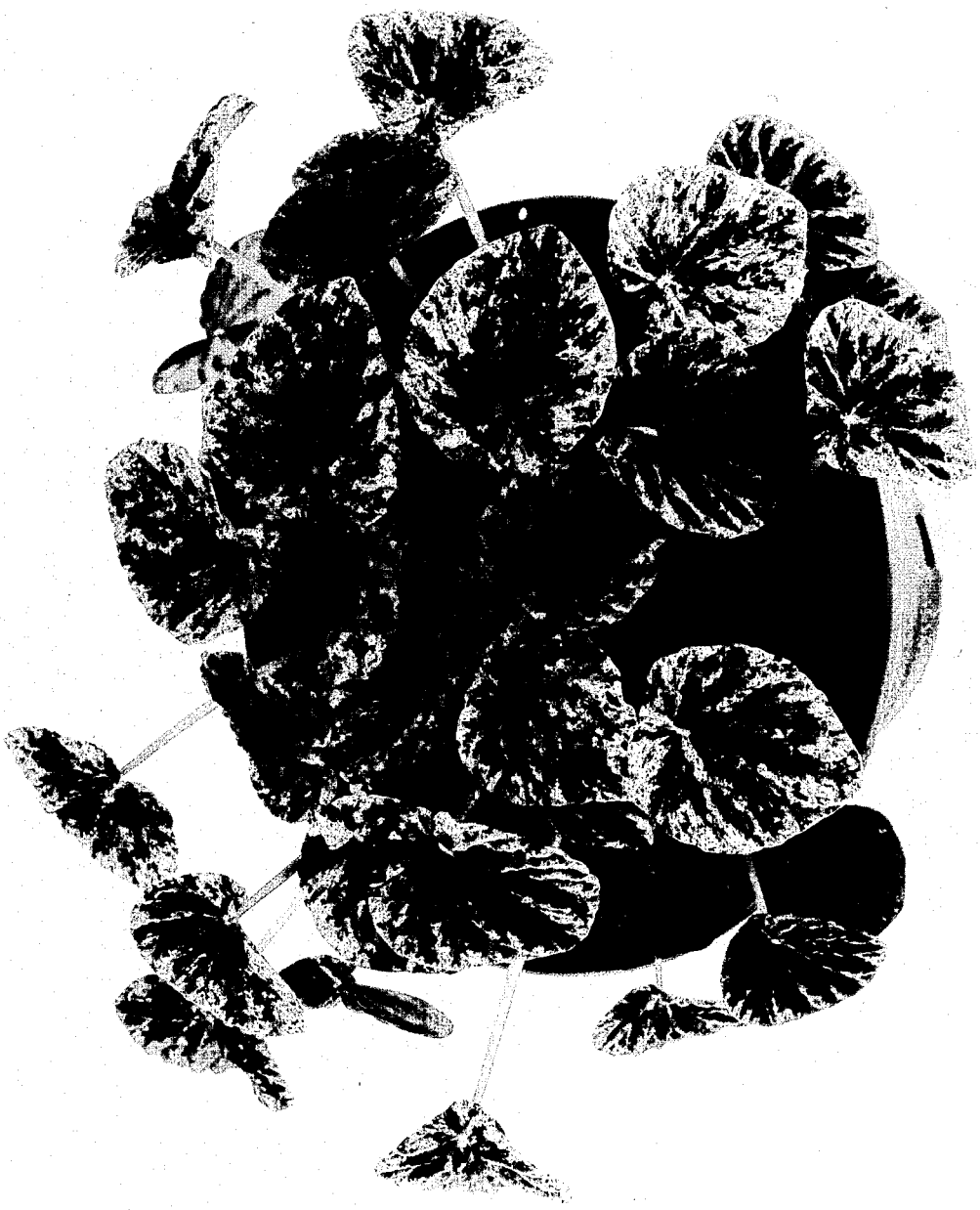

* * * * *